US006271422B1

(12) United States Patent
Bieniarz et al.

(10) Patent No.: US 6,271,422 B1
(45) Date of Patent: Aug. 7, 2001

(54) METHOD FOR FLUOROMETHYLATION OF ALCOHOLS VIA HALOGENATIVE DECARBOXYLATION

(75) Inventors: Christopher Bieniarz, Highland Park; Kornepati V. Ramakrishna, Libertyville; Christopher Behme, Lake Villa, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/587,417

(22) Filed: Jun. 1, 2000

(51) Int. Cl.[7] .................................................. C07C 41/00
(52) U.S. Cl. ........................... 568/683; 568/681; 568/684
(58) Field of Search ..................................... 568/683, 681, 568/684

(56) References Cited

U.S. PATENT DOCUMENTS

| Re. 35,568 | 7/1997 | Halpern et al. ................... 568/683 |
| 3,683,092 | 8/1972 | Regan et al. ..................... 424/342 |
| 4,250,334 | 2/1981 | Coon et al. ....................... 568/683 |
| 4,314,087 | 2/1982 | Radlick ............................. 568/842 |
| 4,469,898 | 9/1984 | Coon et al. ....................... 568/683 |
| 4,847,427 | 7/1989 | Nappa ............................... 568/615 |
| 4,874,901 | 10/1989 | Halpern et al. ................... 568/683 |
| 4,996,371 | 2/1991 | Halpern et al. ................... 568/683 |
| 5,705,710 | 1/1998 | Baker et al. ...................... 568/683 |
| 5,789,630 | 8/1998 | Baker et al. ...................... 570/141 |

OTHER PUBLICATIONS

Kochi, The Mechanism . . . Lead(IV) Acetate, J. American Chem. Society, 87:8, pp. 1811–1812, Apr. 1965.*

* cited by examiner

Primary Examiner—Johann Richter
Assistant Examiner—Elvis O. Price
(74) Attorney, Agent, or Firm—Brian R. Woodworth

(57) ABSTRACT

A method for fluoromethylation of an alcohol via halogenative decarboxylation. The method includes the step of reacting an alcohol of the formula $R^1C(CX_3)_2OH$ with an alpha-haloester of the formula $X^2CH_2CO_2R^2$ to form an alpha-alkoxy ester, wherein $R^1$ is selected from the group consisting of hydrogen and alkyl groups, wherein $R^2$ is selected from the group consisting of hydrogen and alkyl groups, wherein X, at each occurrence, is independently selected from the group consisting of hydrogen, bromine, fluorine, and chlorine, and wherein $X^2$ is selected from the group consisting of bromine and chlorine. The resulting alpha-alkoxy ester is saponified to form an alpha-alkoxy acid which is heated at reflux with lead tetraacetate and a chlorinating agent to form a chloride compound of the formula $R^1C(CX_3)_2OCH_2Cl$. The chloride compound is converted to a fluoride compound of the formula $R^1C(CX_3)_2OCH_2F$ with a fluorinating agent.

11 Claims, 1 Drawing Sheet

METHOD FOR FLUOROMETHYLATION OF ALCOHOLS VIA HALOGENATIVE DECARBOXYLATION

FIELD OF THE INVENTION

The present invention is directed to a method for fluoromethylation of an alcohol. In particular, the present invention is directed to a method in which an alcohol is reacted with an alpha-haloester to form an alpha-alkoxy acid which is then decarboxylatively halogenated to form a chloromethyl ether. The chloromethyl ether is then converted to the desired fluoride by reacting it with a fluorinating agent.

BACKGROUND OF THE INVENTION

Anesthetics belong to a class of biochemical depressant drugs which affect the vital functions of cells. Anesthetics generally produce analgesia, loss of consciousness, diminished reflex activity, and muscular relaxation, with minimal depression of the vital functions. Anesthetics may be gaseous (volatile) or fixed (non-volatile). Gaseous anesthetics are inhaled and enter the bloodstream through the lungs while fixed anesthetics are administrated parenterally or through the alimentary canal.

Many currently used gaseous anesthetics are halogenated compounds. These compounds tend to cause less metabolic disturbance and are less flammable than traditional gaseous anesthetic compounds such as ether and cyclopropane. Examples of halogenated anesthetic compounds include halothane ($CF_3CHBrCl$) and trichloroethylene ($Cl_2C=CHCl$) as well as halogenated ether compounds such as enflurane ($CHF_2OCF_2CHClF$), fluroxene ($CF_3CH_2OCH=CH_2$), methoxyflurane ($Cl_2CHCF_2OCH_3$) and isoflurane ($CF_3CHClOCHF_2$).

A particularly useful halogenated ether anesthetic is sevoflurane, $(CF_3)_2CHOCH_2F$, also known as 2-(fluoromethoxy)-1,1,1,3,3,3,-hexafluoropropane or fluoromethyl-1,1,1.3.3,3-hexafluoro-2-propyl ether. Sevoflurane is today one of the most important and widely used general anesthetics. Sevoflurane combines various characteristics that are most desirable in an inhalation anesthetic, including the lowest blood/gas partition coefficient of 0.63, smooth induction and recovery from anesthesia, minimal irritation to the upper respiratory tract, low metabolic rate, and rapid elimination. In addition, sevoflurane is suitable for out-patient surgery use. Although sevoflurane's definitive mechanism of action has not been elucidated, it has recently been shown that sevoflurane interacts with nicotinic acetylcholine receptors by affecting the open and closed state of the ion channels at clinical and lower concentrations. Sevoflurane may also effect reversible modulation of GABA and glycine receptors. The above suggest that at least part of the anesthetic action of sevoflurane may be due to interactions between sevoflurane and specific voltage-gated ion channels.

The preparation of fluorinated compounds such as sevoflurane tends to be difficult because of the limited number of selective fluorination reactions available. Direct fluorination of organic compounds to replace hydrogen is statistical, non-selective, and generally accompanied by the formation of many side products. Hence, fluorinated compounds are usually prepared by first synthesizing a substituted organic intermediate. wherein the substituent group is at the site to be fluorinated, and then displacing the substituent group with a fluoride ion. Metal fluorides, for example, have been used to displace chlorine substituent groups.

Several synthetic routes to sevoflurane employ hexafluoroisopropyl alcohol (HFIP) as a starting material. For example, U.S. Pat. No. 3,683,092 discloses a method for synthesizing sevoflurane involving the methylation of hexafluoroisopropyl alcohol followed by fluorination with either (a) bromine trifluoride, or (b) chlorine gas, followed by potassium fluoride. U.S. Pat. No. 4,469,898 discloses a method for synthesizing sevoflurane which includes the mixing of hexafluoroisopropyl alcohol, formaldehyde, hydrogen fluoride, and a protonating, dehydrating and fluoride ion generating agent. U.S. Pat. No. 4,250,334 discloses a method for synthesizing sevoflurane by adding HFIP to a mixture of a stoichiometric excess of paraformaldehyde and hydrogen fluoride, plus sufficient sulfuric acid to sequester most of the water produced by the reaction. U.S. Pat. No. 4,314,087 discloses a method for synthesizing sevoflurane by reacting HFIP with hydrogen fluoride and a formaldehyde.

The routes disclosed in the referenced patents can result in unwanted by-products which may be difficult to separate from sevoflurane produced by the synthesis. Moreover, the use of corrosive materials in these synthetic routes requires specialized equipment and special handling precautions.

Other methods used to make hexafluoroisopropyl ethers include the conversion of 1,1,1,3,3,3-hexachloroisopropyl ethers to 1,1,1,3,3,3-hexafluoroisopropyl ethers. For example, methyl 1,1,1,3,3,3-hexachloroisopropyl ether and chloromethyl 1,1,1,3,3,3-hexachloroisopropyl ether can be converted to sevoflurane by reaction of each of the above compounds with bromine trifluoride. Hexafluoroisopropyl ethers also can be made by reacting each of these chlorinated compounds with hydrogen fluoride, followed by reaction with bromine trifluoride. U.S. Pat. No. 4,874,901 discloses a method for fluorinating halogenated ether compounds, wherein compounds such as sevoflurane can be prepared by reacting chloromethyl hexafluoroisopropyl ether with either potassium fluoride or sodium fluoride. However, the chlorine replacement methods are not desirable because large volumes of chloride are released in the synthetic process, the yields are low, and multiple chloro-fluoro intermediates are formed. The intermediates must be removed to obtain the final ether product, sevoflurane. The purification processes increase the difficulty and cost of synthesis of 1,1,1,3,3,3-hexafluoroisopropyl ethers by these methods.

Hexafluoropropanes alternatively have been synthesized from malononitrile in the presence of bromine trifluoride, as disclosed in U.S. Pat. Nos. 5,789,630 and 5,705,710.

Another potential route to sevoflurane is by fluorodecarboxylation. Patrick et al., *J Org. Chem.* 48, 4158–4159 (1983), reports that alkyl carboxylic acids can undergo fluorodecarboxylation with xenon difluoride ($XeF_2$) in the presence of hydrogen fluoride. Although the use of xenon difluoride on a small scale can be effective, the cost of xenon difluoride makes its use impractical on a large scale. Furthermore, when alkoxyacetic acids are fluorodecarboxylated with xenon difluoride, significant amounts of side products are formed. Replacement of a carboxylic acid group with a fluorine group has also been disclosed in U.S. Pat. No. 4,996,371 and in Pat. No. RE 35,568 which teach a reaction of hydrogenated aliphatic carboxylic acid compounds with bromine trifluoride; and in U.S. Pat. No. 4,847,427, which teaches a method for preparing fluorocarbon polyethers by neutralizing a perfluorinated carboxylic acid by heating with fluorine in the presence of metal fluoride to replace the carboxylic acid group.

While the above-discussed methods are useful for preparing certain fluorinated compounds, these methods can be complex, expensive, and often provide fluorinated products in low yield together with considerable amounts of side products. Hence there is a need for improved procedures for the preparation of fluorinated compounds.

The present invention provides an improved procedure for the preparation of fluorinated compounds, including sevoflurane and other fluorinated anesthetics.

It is an object of the present invention to provide a method for the preparation of fluorine-containing organic compounds. Still a further object is to provide a method whereby a fluorine-containing organic compound may be prepared from a partially chlorinated, brominated, or iodinated organic compound. An additional object is to provide a method for preparing a fluorine containing organic compound whereby the formation of undesirable decomposition or side products is substantially avoided.

SUMMARY OF THE INVENTION

The invention is directed to a novel method for fluoromethylation of an alcohol via halogenative decarboxylation. The method includes the steps of:

(a) reacting an alcohol of the formula $R^1C(CX_3)_2OH$ with an alpha-haloester of the formula $X^2CH_2CO_2R^2$ under basic conditions in the presence of a first solvent to form an alpha-alkoxyester, wherein $R^1$ is either hydrogen or an alkyl group. wherein $R^2$ is either hydrogen or an alkyl group, wherein X, at each occurrence, is independently selected from the group consisting of hydrogen, chlorine, bromine, or fluorine, and wherein $X^2$ is selected from the group consisting of bromine and chlorine;

(b) saponifying the alpha alkoxyester to form an alpha-alkoxy acid;

(c) refluxing the alpha-alkoxy acid with lead tetraacetate and a chlorinating agent in the presence of a second solvent to form a chloride compound of the formula $R^1C(CX_3)_2OCH_2Cl$; and (d) converting the chloride compound to a fluoride compound of the formula $R^1C(CX_3)_2OCH_2F$ with a fluorinating agent in the presence of a third solvent. In another aspect, the invention is directed to a method for synthesizing sevoflurane by:

(a) reacting 1,1,1,3,3,3-hexafluoroisopropanol with an alpha-haloester of the formula $X^2CH_2CO_2R^2$ under basic conditions in a first solvent to form an alpha-alkoxy ester, wherein $R^2$ is either hydrogen or an alkyl group, and wherein $X^2$ is selected from the group consisting of bromine and chlorine;

(b) saponifying the alpha-alkoxy ester to a carboxylic acid;

(c) halogenatively decarboxylating the carboxylic acid with lead tetraacetate and a chlorinating agent in a second solvent to form sevochlorane; and (d) converting sevochlorane to sevoflurane with a fluorinating agent in the presence of a third solvent.

DETAILED DESCRIPTION OF THE INVENTION

Figure 1:
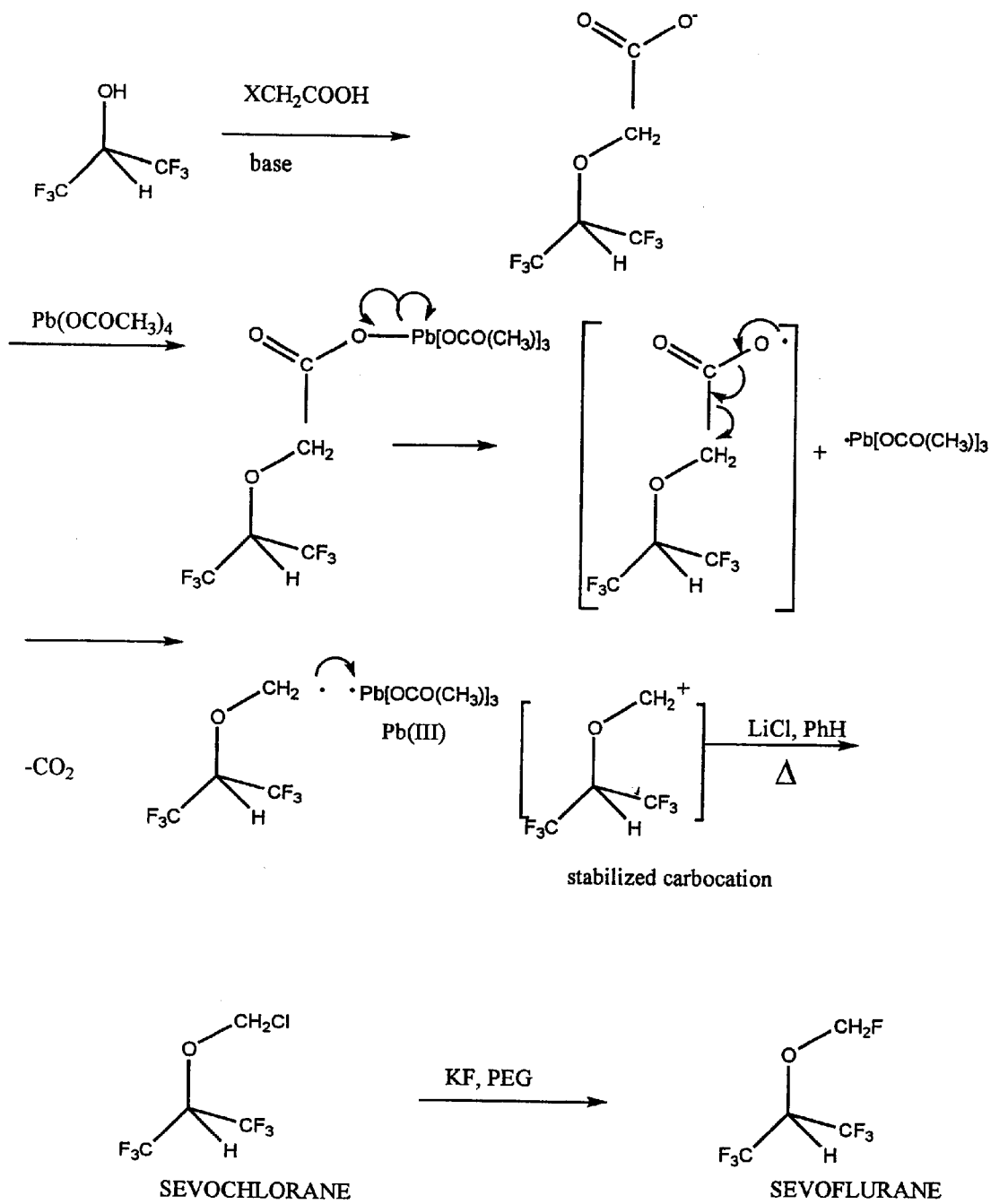
FIG. 1 depicts an embodiment of the reaction of the present invention.

As used herein, the term "alkyl" means straight or branched, saturated or unsaturated carbon chains having up to 10, preferably up to 6 and more preferably up to 4 carbon atoms. This term is also meant to encompass alkenyl and alkynyl groups.

As used herein, "hexafluoroisopropanol" and "HFIP" mean 1,1,1,3,3,3-hexafluoroisopropyl alcohol. As used herein, "sevochlorane" means a compound of the formula $(CF_3)_2CHOCH_2Cl$.

In accordance with the method of the present invention, an alcohol of the general formula $R^1C(CX_3)_2OH$, e.g., hexafluoroisopropanol, is reacted with a halide of the general formula $X^2CH_2CO_2R^2$, e.g., ethyl bromoacetate, under basic conditions in the presence of a first solvent to form an alpha-alkoxy ester. In this reaction, $R^1$ is hydrogen or an alkyl group, and $R^2$ is hydrogen or an alkyl group. In a preferred embodiment, $R^2$ is an alkyl group. X, at each occurrence, is independently selected from the group consisting of hydrogen, bromine, fluorine, and chlorine. $X^2$ is selected from the group consisting of bromine and chlorine. The resulting alpha-alkoxy ester is then saponified to form an alpha-alkoxy acid. For example, saponification of the alpha-alkoxy ester preferably is achieved by heating with aqueous LiOH. The alpha-alkoxy acid is then heated at reflux with lead tetraacetate and a chlorinating agent, e.g., lithium chloride, in the presence of a second solvent, e.g., benzene, to form a chloromethyl ether of the formula $R^1C(CX_3)_2OCH_2Cl$. Finally, the chloromethyl ether is converted to a fluoride compound of the formula $R^1C(CX_3)_2OCH_2F$ by reacting it with a fluorinating agent in the presence of a third solvent.

In another aspect, the present invention is directed to a method for synthesizing sevoflurane from HFIP, as set forth in FIG. 1. In this reaction, hexafluoroisopropanol is reacted with an alpha-haloester of the formula $X^2CH_2CO_2R^2$ under basic conditions in the presence of a first solvent to form an alpha-alkoxy ester. In this reaction, $R^2$ is an alkyl group and $X^2$ is selected from the group consisting of bromine and chlorine. The resulting ester is then saponified to a carboxylic acid which is then halogenatively decarboxylated with lead tetraacetate and a chlorinating agent in the presence of a second solvent to form sevochlorane. The resulting sevochlorane is then reacted with a fluorinating agent in the presence of a third solvent to form sevoflurane.

One of ordinary skill will appreciate that a variety of known fluorinating agents can be used in connection with the methods of the present invention. For example, KF can be used to fluorinate the chloromethyl ether compounds in accordance with the methods of the present invention.

One of ordinary skill also will appreciate that a variety of known chlorinating agents can be used in connection with the methods of the present invention. For example, lithium chloride or sodium chloride can be used in accordance with the method of the present invention.

As above-indicated, ethyl bromoacetate can be used in accordance with the method of the present invention. However, one of ordinary skill in the art will appreciate that other alpha-haloesters can be used efficaciously in accordance with the reactions of the present invention. For example, methyl bromoacetate may also be utilized as an alpha-haloester in connection with the reactions of the present invention.

Suitable first solvents include tetrahydrofuran (THF) and diethyl ether.

Suitable second solvents include aromatic solvents such as benzene. Other appropriate second solvents include 1,4-dioxane.

The third solvent may have the formula HO—$(CH_2CH_2O)_n$H wherein n is an integer from one to twenty, and preferably n is an integer of from eight to ten. A presently preferred third solvent is PEG400, i.e., a polyethylene glycol having an average molecular weight of 400.

The basic conditions of the method can be obtained by a variety of suitable methods known to those skilled in the art. For example, NaH can be added to the reaction mixture.

Saponification of the alpha alkoxycarboxy anion in accordance with the reaction of the present invention may be performed by a variety of suitable methods known to those skilled in the art. For example, the substrate can be saponified by heating with aqueous LiOH.

The following examples are presented for illustrative purposes only, and are not intended to limit the scope of the invention, which is as defined in the claims below. All analyses were conducted by gas chromatography. All percentages are by mole percent.

EXAMPLE 1

Alpha-(hexafluoroisopropoxy)acetic acid was synthesized in the following manner as shown in Reaction Scheme I.

Reaction Scheme I

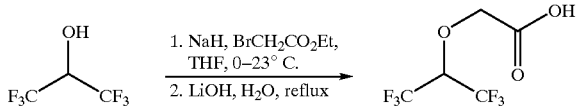

Into a flame-dried 250 mL round-bottomed flask was placed dry sodium hydride (2.4 g, 100 mmol) and 100 mnL of anhydrous tetrahydrofuran. The resultant slurry was maintained under a nitrogen atmosphere while cooling to 0° C. in an ice bath. To this slurry was added 1,1,1,3,3,3-hexafluoroisopropanol (11.6 mL, 110 mmol) dropwise while stirring. The pre-formed alkoxide was stirred for an additional 15 minutes before adding ethyl bromoacetate (11.1 mL, 100 mmol) in a single portion. The mixture was allowed to warm gradually to ambient temperature while stirring overnight. The reaction mixture was filtered and concentrated in vacuo. The resultant crude ester was heated for two hours at reflux in water (100 mL) with an equivalent of LiOH (4.2 g, 100 mmol) added. The reaction mixture was cooled and IN aqueous KOH solution added, bringing the pH to >13. The basic solution was extracted with ether (2×75 mL) and then acidified to pH 1 with concentrated HCl. The product was extracted with $CH_2Cl_2$ (3×75 mL), dried over $Na_2SO_4$, filtered, and concentrated in vacuo to afford 15.0g (66%) of the a-alkoxy acid as a white solid.

EXAMPLE 2

Sevochlorane was synthesized via decarboxylative halogenation (according to the procedure of Kochi, J. K. *J Am. Chem. Soc.* 1965, 87, 1811) as follows, as shown in Reaction Scheme II.

Reaction Scheme II

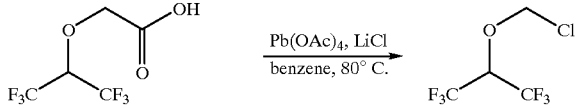

To a solution of a-(hexafluoroisopropoxy)acetic acid (4.90 g, 21.7 mol) dissolved in anhydrous benzene (43 mL) was added lead tetraacetate (10.11 g, 21.7 mmol) and then lithium chloride (919 mg, 21.7 mmol), and the mixture was sparged with dry nitrogen for 10 minutes. The degassed reaction mixture was heated at reflux for 20 minutes until the initial cloudy yellow slurry had become a clear solution with a gummy white precipitate, and gas evolution had ceased. GC/MS analysis of the crude reaction mixture showed sevochlorane to be the major product along with a small amount of methyl chloride and minor impurities. The product was distilled directly from the reaction mixture at a temperature of 77–78° C. as a co-distillate with benzene. The product solution was used directly in the subsequent conversion to sevoflurane.

EXAMPLE 3

Sevoflurane was synthesized in the following manner, as shown in Reaction Scheme III.

Reaction Scheme III

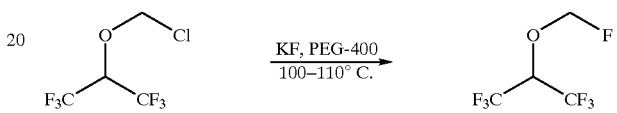

The sevochloranelbenzene distillate from the previous procedure (Example 2) was combined with PEG-400 (43 mL) and 5 equivalents of KF (6.3 g, 0.11 mol) and heated at 100–110° C. for two hours. The product was distilled directly from the reaction flask to afford 1.2 g (28% for two steps) of sevoflurane.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

What is claimed is:

1. A method for fluoromethylation of an alcohol comprising steps of:
    reacting an alcohol of the formula $R^1C(CX_3)_2OH$ with an alpha-haloester of the formula $X^2CH_2CO_2R^2$ to form an alpha-alkoxy ester, wherein Ri is selected from the group consisting of hydrogen and alkyl groups, wherein R2 is selected from the group consisting of hydrogen and alkyl groups, wherein X, at each occurrence, is independently selected from the group consisting of hydrogen, bromine, fluorine, and chlorine, and wherein $X^2$ is selected from the group consisting of bromine and chlorine, wherein said step of reacting is conducted in the presence of a solvent and wherein said solvent is selected from the group consisting of an ether and tetrahydrofuran;
    saponifying said alpha-alkoxy ester to form an alpha-alkoxy acid;
    heating at reflux said alpha-alkoxy acid with lead tetraacetate and a chlorinating agent to form a chloromethyl ether of the formula $R^1C(CX_3)_2OCH_2Cl$; and
    converting said chloromethyl ether to a fluoride compound of the formula $R^1C(CX_3)_2OCH_2F$ with a fluorinating agent.

2. A method in accordance with claim 1, wherein said fluorinating agent is KF.

3. A method in accordance with claim 1, wherein said chlorinating agent is lithium chloride.

4. A method in accordance with claim 1, wherein said step of reacting an alcohol with an alpha-haloester is conducted under basic conditions.

5. A method in accordance with claim 1, wherein said step of heating at reflux is conducted in the presence of a second solvent selected from the group consisting of benzene and dioxane.

6. A method in accordance with claim 1, wherein said step of converting said chloromethyl ether to a fluoride compound is conducted in the presence of a third solvent.

7. A method in accordance with claim 6, wherein said third solvent has a formula HO—$(CH_2CH_2O)_n$H wherein n is an integer from one to twenty.

8. A method for synthesizing sevoflurane comprising the steps of:

reacting 1,1,1,3,3,3-hexafluoroisopropanol with an alpha-haloester of the formula $X^2CH_2CO_2R^2$ to form an alpha-alkoxy ester, wherein $R^2$ is an alkyl group, and wherein $X^2$ is selected from the group consisting of bromine and chlorine;

saponifying said ester to a carboxylic acid;

halogenatively decarboxylating said carboxylic acid with lead tetraacetate and a chlorinating agent to form sevochlorane; and converting sevochlorane to sevoflurane with a fluorinating agent.

9. A method in accordance with claim 8, wherein said alpha-haloester is ethyl bromoacetate.

10. A method in accordance with claim 8, wherein said fluorinating agent is KF.

11. A method in accordance with claim 8, wherein said chlorinating agent is lithium chloride.

* * * * *